(12) United States Patent
Dickie

(10) Patent No.: US 8,522,797 B2
(45) Date of Patent: Sep. 3, 2013

(54) ACCESSORY HEAD FOR A POWERED TOOTHBRUSH AND TOOTHBRUSH INCORPORATING THE SAME

(75) Inventor: Robert G. Dickie, King City (CA)

(73) Assignee: Brushpoint Innovations Inc, King City, Ontario (CA)

( * ) Notice: Subject to any disclaimer, the term of this patent is extended or adjusted under 35 U.S.C. 154(b) by 89 days.

(21) Appl. No.: 12/842,097

(22) Filed: Jul. 23, 2010

(65) Prior Publication Data
US 2012/0021382 A1 Jan. 26, 2012

(51) Int. Cl.
*A61C 15/00* (2006.01)
*A61C 17/22* (2006.01)
*A45D 44/18* (2006.01)

(52) U.S. Cl.
USPC ............ 132/322; 132/309; 15/22.1; 433/216

(58) Field of Classification Search
USPC .................. 132/309, 322, 120, 226, 73, 73.6; 601/139, 141, 161–165; 15/22.1; 81/491; 433/143, 147
See application file for complete search history.

(56) References Cited

U.S. PATENT DOCUMENTS

| | | | | |
|---|---|---|---|---|
| 822,928 A * | 6/1906 | Delano | ........................... | 15/105 |
| 1,039,235 A * | 9/1912 | Wiggins | ........................ | 433/143 |
| 3,183,538 A * | 5/1965 | Hubner | ........................... | 15/22.1 |
| 5,224,502 A * | 7/1993 | Walker, Jr. | ..................... | 132/325 |
| 6,691,716 B2 * | 2/2004 | Neuner et al. | ................ | 132/218 |
| 7,055,531 B2 | 6/2006 | Rehkemper | | |
| 7,311,108 B2 | 12/2007 | Getgey et al. | | |
| 2005/0000537 A1 * | 1/2005 | Junkins | ......................... | 132/309 |
| 2005/0189000 A1 * | 9/2005 | Cacka et al. | .................. | 132/322 |
| 2006/0283886 A1 * | 12/2006 | Keller | ........................... | 222/137 |
| 2007/0204878 A1 * | 9/2007 | Apotheker et al. | ........... | 132/322 |

* cited by examiner

Primary Examiner — Nicholas Lucchesi
Assistant Examiner — Niyati D Shah
(74) Attorney, Agent, or Firm — Sand & Sebolt

(57) ABSTRACT

A replaceable accessory head for a powered toothbrush. The user selects one of a plurality of dental care accessory assemblies for flossing, brushing teeth, or for stimulating the gums. That assembly is engaged with the head which in turn is engaged with the handle and is locked thereto. This locking motion also causes the assembly to become locked to the head and the assembly may then be used for its intended purpose. A vibratory mechanism in the handle is activated causing vibration in the accessory assembly and thus improving the flossing, brushing or gum stimulation motions. When the assembly is worn out or when a different dental hygiene task is to be undertaken, the user detaches the head from the handle, thereby simultaneously unlocking the accessory assembly from the head. The assembly is then disengaged and is replaced by a different accessory assembly.

22 Claims, 16 Drawing Sheets

ACCESSORY HEAD FOR A POWERED TOOTHBRUSH AND TOOTHBRUSH INCORPORATING THE SAME

BACKGROUND OF THE INVENTION

1. Technical Field

This invention generally relates to powered toothbrushes. More particularly, the invention relates to an electric or sonic toothbrush that includes a handle and a detachable head. Specifically, the invention relates to a head for a powered toothbrush that includes replaceable accessory assemblies which are each selectively engageable and lockable with the head to perform a different dental hygiene task.

2. Background Information

Research is showing that dental hygiene contributes more to a person's health than just simply keeping their teeth looking good. Poor dental habits may contribute to the development of heart disease, increase the risk of stroke, may play a role in low birth weight in babies, and pose serious health risks to people with diabetes.

Dental hygiene includes more than just brushing teeth. Flossing regularly, stimulating the gums, cleaning the tongue and other such dental habits all aid in keeping a person's teeth as healthy as possible.

There are a variety of different implements that a person can use to care for their teeth. These implements tend to be manually operable. For example, floss is a thin ribbon of plastic or nylon that is cut to a desired length and then positioned between a pair of adjacent teeth. The floss is manually scraped up and down along the sides of the teeth in order to remove food or dental plaque from between the teeth. Alternatively, the user can utilize a floss pick to floss between their teeth. A floss pick is an implement that includes a U-shaped head with a length of floss disposed between the tips of the arms on the head. The head is inserted into the mouth in such a way that the floss is gently inserted between the teeth. The handle of the floss pick is then manually manipulated so that the floss scrapes along the sides of the teeth.

In a similar fashion, a person may utilize an interdental or interproximal brush or an end-tufted brush to remove food and dental plaque from between the teeth. These types of brushes include a head with a small pointed-tip brush. The user positions the brush so that the bristles are disposed in the appropriate location between a pair of adjacent teeth and then the brush handle is manipulated to move the interdental brush up and down and in and out to remove the food or plaque between the teeth.

Gum stimulators are tools that comprise a handle with a rubber tip at one end. The rubber tip is placed in contact with the tooth and the user then manually moves the handle of the stimulator so that the tip is moved in circles on the surface of the tooth. The tip is also moved back-and-forth along the gum line. This device aids in removing plaque and food particles but also stimulates and massages the gum, bringing increased blood flow to the same.

While all of these implements work adequately, there is still a need in the art for an improved device that enables a user to more quickly and efficiently floss and brush the teeth, and more easily stimulate the gums to promote improved oral health.

SUMMARY OF THE INVENTION

The device of the present invention is a replaceable accessory head for a powered toothbrush. The user selects one of a plurality of dental care accessory assemblies for flossing, brushing teeth, or for stimulating the gums. That assembly is engaged with the head, which in turn is engaged with the handle and is locked thereto. This locking motion also causes the assembly to become locked to the head and the assembly may then be used for its intended purpose. A vibratory mechanism in the handle is activated causing vibration in the accessory assembly and thus improving the flossing, brushing or gum stimulation motions. When the assembly is worn out or when a different dental hygiene task is to be undertaken, the user detaches the head from the handle, thereby simultaneously unlocking the accessory assembly from the head. The assembly is then disengaged and is replaced by a different accessory assembly.

The head, handle, and a plurality of accessory assemblies may be sold as a kit for undertaking several dental hygiene tasks. The accessory assemblies include, but are not limited to a floss pick, a gum stimulator, an interdental brush and a tongue scraper. The kit allows the user to more rapidly and efficiently perform a variety of powered dental hygiene tasks.

BRIEF DESCRIPTION OF THE DRAWINGS

The preferred embodiments of the invention, illustrative of the best mode in which applicant has contemplated applying the principles, are set forth in the following description and are shown in the drawings and are particularly and distinctly pointed out and set forth in the appended claims.

DETAILED DESCRIPTION OF THE INVENTION

Figure 1:
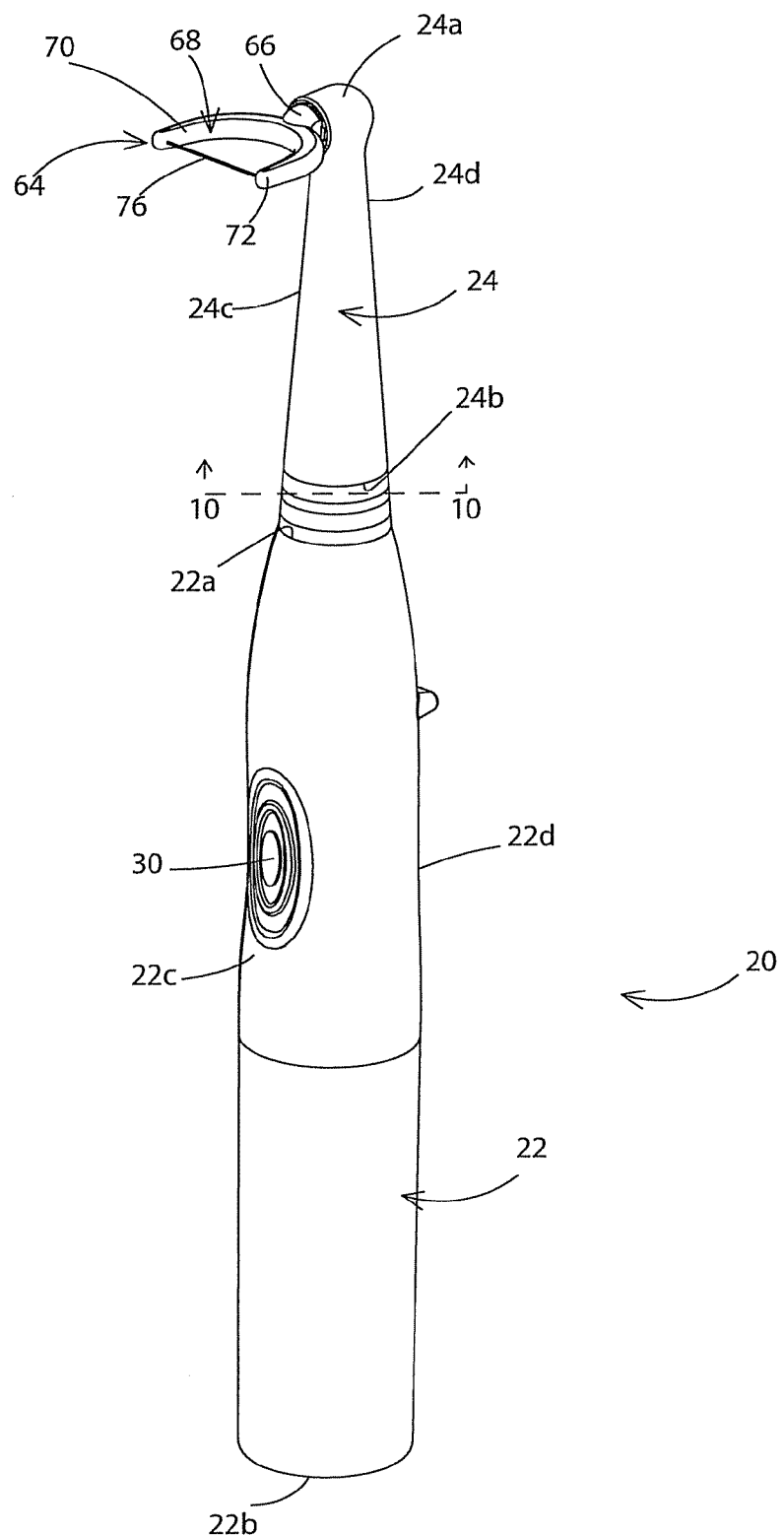
FIG. 1 is a perspective view of a sonic toothbrush in accordance with the present invention and showing a first accessory head attached thereto, where the accessory head is a flossing head.

Referring to FIGS. 1-13 there is shown a sonic toothbrush in accordance with the present invention and generally indicated at 20. Brush 20 comprises a handle 22 and an accessory head 24.

Handle 22 has a top end 22a, a bottom end 22b, a front face 22c and a rear face 22d. Handle 22 defines an interior cavity 26 that preferably houses a power source, such as one or more batteries 28. An activation button 30 is provided in front face 22c of handle 22. Button 30 is depressed to switch the brush on and off.

An attachment member 32 (FIG. 2) extends outwardly from top end 22a of handle 22. Attachment member 32 has a top end 32a, a bottom end 32b (FIG. 3), a front face 32c and a rear face 32d. Attachment member 32 tapers from proximate bottom end 32b toward top end 32a thereof. A first lock member 34 (FIG. 2) extends outwardly from front face 32c of attachment member 32 and a second look member 35 extends outwardly from rear face 32d thereof. First and second lock members 34, 35 are therefore opposed to each other. First and second lock members 34, 35 are spaced a distance from the bottom end 32b of attachment member 32 such that a recessed region 36 is defined between lock members 34, 35 and top end 22a of handle 22. Lock members 34, 35 are provided to enable head 24 to be secured to handle 22 bayonet-style, by requiring the rotation of the head 24 through approximately a ¼ turn relative to the handle 24 as will be hereinafter described.

Figure 8:
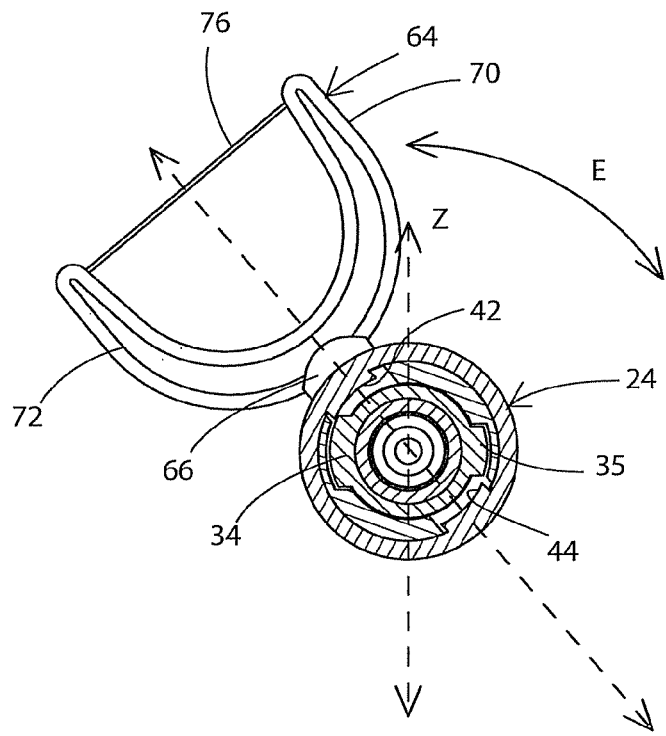
FIG. 8 is a cross-sectional view of the head taken through line 10-10 of FIG. 1, and showing the head in the engaged but not yet locked position.
Figure 9:
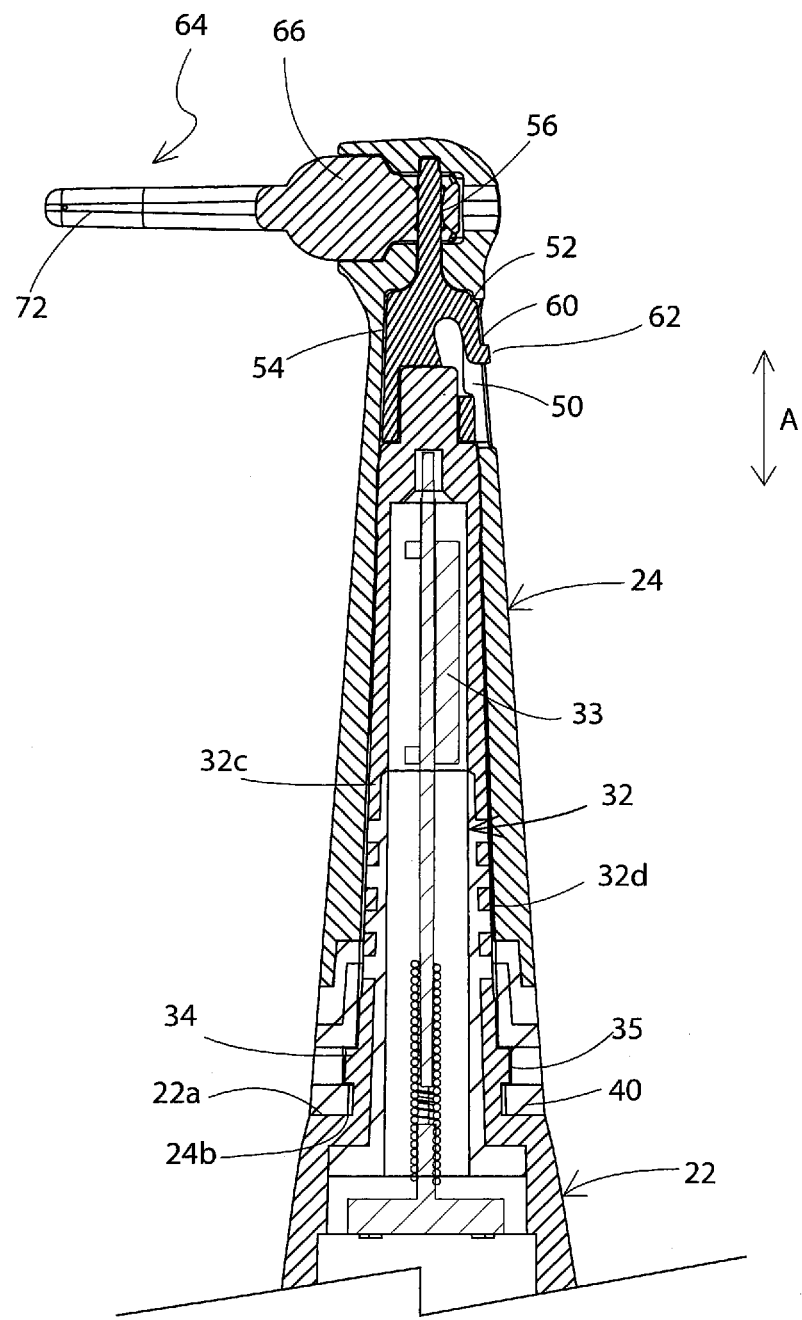
FIG. 9 is a cross-sectional side view of the sonic brush with the head locked to the handle and the flossing attachment locked to the head.

FIG. 8 shows that lock member 34 is of different dimensions to larger than lock member 35. The difference in size ensures that head 24 can only engage with handle 22 in one orientation. (It will be understood that, alternatively, lock member 34 could be smaller than lock member 35 without departing from the spirit of the present invention.)

Although not shown in detail herein, attachment member 32 includes a motor, a drive shaft and any suitable mechanism 33 (FIGS. 2 & 9) for generating a vibration in the head 24 of brush 20. The vibratory mechanism 33 may be designed to vibrate any portion of head 24, but most particularly, is suitable for generating a vibration in any one of a number of dental accessory assemblies as will be hereinafter described. Preferably, the vibratory mechanism 33 is one that will vibrate in a direction aligned with the longitudinal axis "Y" (FIG. 2) of brush 20. In other words, the vibratory mechanism vibrates 33 in an up and down motion as indicated by the arrows "A" shown in FIG. 9.

Head 24 has a top end 24a, a bottom end 24b, a front face 24c and a back face 24d. Head 24 defines an interior bore 38 that is complementary in shape to attachment member 32. Bore 38 is wider proximate bottom end 24b of head 24 and tapers toward top end 24a thereof. The interior surface of the exterior wall of head 24 defines an annular lock member 40 proximate bottom end 24b thereof. A first recess 42 is provided in the interior surface adjacent lock member 40 and is complementary in size to first lock member 34. A second recess 44 is provided in the interior surface opposite first recess 42. Second recess 44 is complementary in size and location to second lock member 35. Lock member 40 is complementary to recess 36 on attachment member 32. It will be understood that the first and second lock members 34, 35 and first and second recesses 42, 44 could be located in other positions on the exterior surface of attachment member 32 and interior surface of head 24 without departing from the spirit of the present invention. Additionally, first and second lock members 34, 35 and the associated first and second recesses 42, 44, do not have to be situated opposite each other but could merely be positioned a distance apart from each other. However, the opposed positions are favored because, when engaged, they will lock head 24 and handle 22 together more uniformly. Furthermore, it will be understood that the first and second lock members could be provided on the interior surface of head 24 and the first and second recesses could be provided on the exterior surface of handle 22 without departing from the spirit of the present invention.

In accordance with yet another feature of the present invention, a slot 46 (FIG. 2) is defined in top end 24a of head 24. Slot 46 is oriented substantially at right angles to the longitudinal axis "Y" of head 24 and handle 22. A channel 48 is defined in top end 24a of head. Channel 48 is a narrowed region of interior bore 38 and is disposed generally aligned with longitudinal axis "Y". Channel 48 intersects slot 46 and extends for a short distance beyond an uppermost region of slot 46. Rear face 24d of head 24 further defines an aperture 50 therein. Aperture 50 is spaced a distance downwardly from top end 24a but is positioned closer to top end 24a than bottom end 24b of head 24.

In accordance with yet another feature of the present invention, a locking assembly 52 is positioned in interior bore 38 of head 24 proximate top end 24a thereof. Locking assembly 52 comprises a base 54 and a locking pin 56. Base 54 defines a longitudinally aligned cavity 58 that is complementary shaped and sized to receive top end 32a of attachment member 32 therein. Lock pin 56 is complementary sized to be received through channel 48. Base 54 further includes a flexible member 60 that has a foot 62 on a free end thereof. Locking assembly 52 is reciprocally slidable in interior bore 38. When locking assembly 52 slides upwardly to a sufficient degree such that top end 32a of attachment member 32 is retained within cavity 58 of locking assembly 52, then foot 62 extends at least partially outwardly through aperture 50 in rear face 24d of head 24.

In accordance with yet another feature of the present invention, a removable dental accessory assembly 64 is provided and is engageable with head 24 preferably proximate top end 24a thereof. FIGS. 1-13 illustrate the accessory assembly 64 as a floss hoop, which will hereafter be referred to by the reference character 64. Floss hoop 64 includes a base 66 and a U-shaped floss holder 68 comprising first and second arms 70, 72. At least a portion of base 66 is complementary to slot 46 in head 24. The portion of the base 66 receivable in slot 46 also defines a hole 74 therein. When base 66 is inserted into slot 46, hole 74 is positioned to be aligned with channel 48 and is sized to receive locking pin 56 there through. Floss hoop 64 includes a length of dental floss 76.

Brush 20 is assembled and used in the following manner. It should be understood that dental accessory assembly 64 may be engaged with head 24 prior to head 24 being engaged with handle 22, or head 24 may be engaged with handle 22 and then dental accessory assembly 64 may be engaged with head 24. The following description will follow the first scenario.

Figure 2:
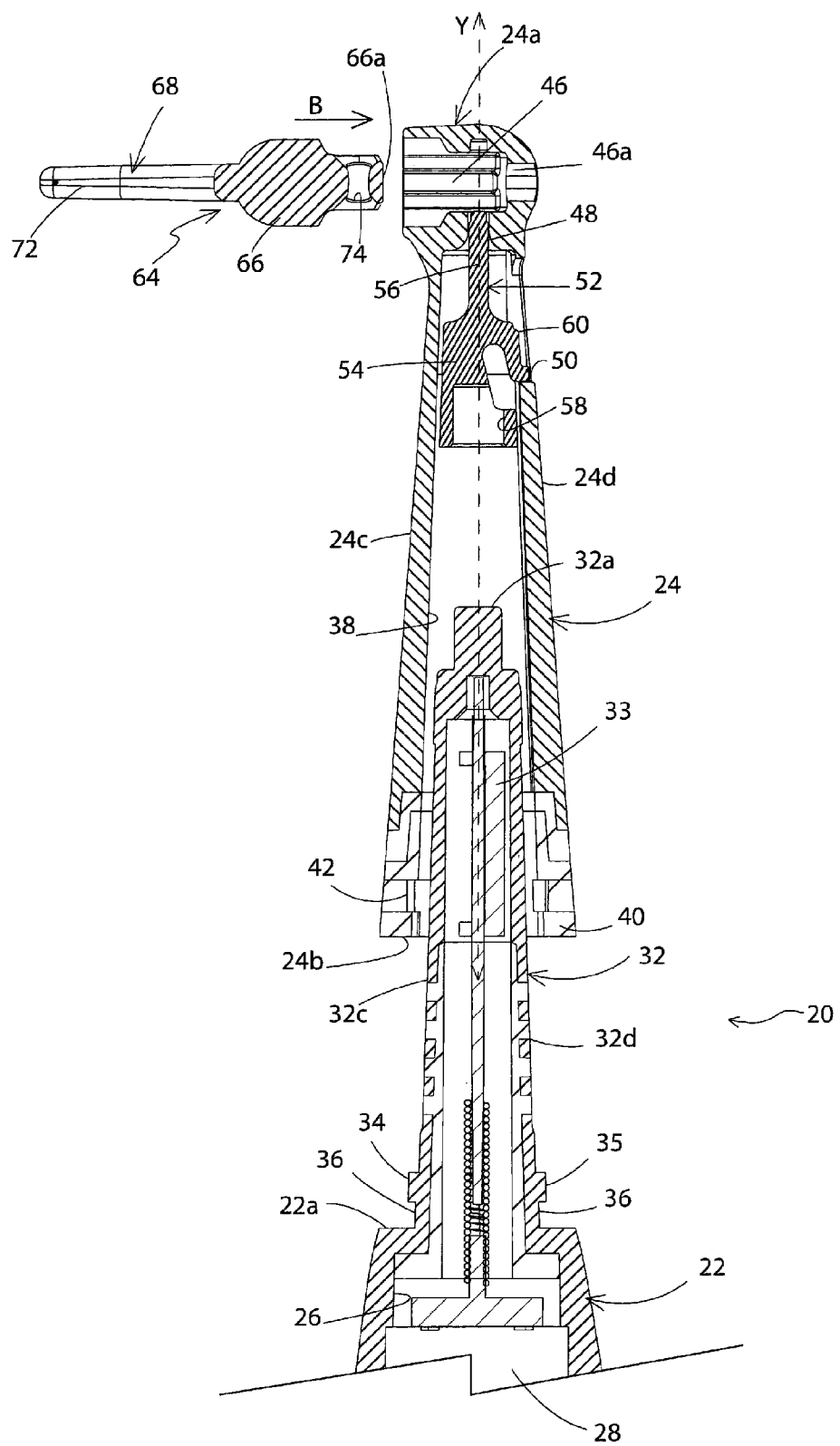
FIG. 2 is a cross-sectional side view of the sonic brush in accordance with the present invention, showing the head disengaged from the handle and the replaceable flossing attachment disengaged from the head.

The user selects floss hoop 64 and inserts a portion of base 66 into slot 46 in the manner indicated by arrow "B" in FIG. 2. When the end 66a of base 66 abuts the interior wall 46a of slot 46, then hole 74 in base 66 is aligned with channel 48. At this point, floss hoop 64 is engaged with head 24 but is not locked thereto.

Figure 3:
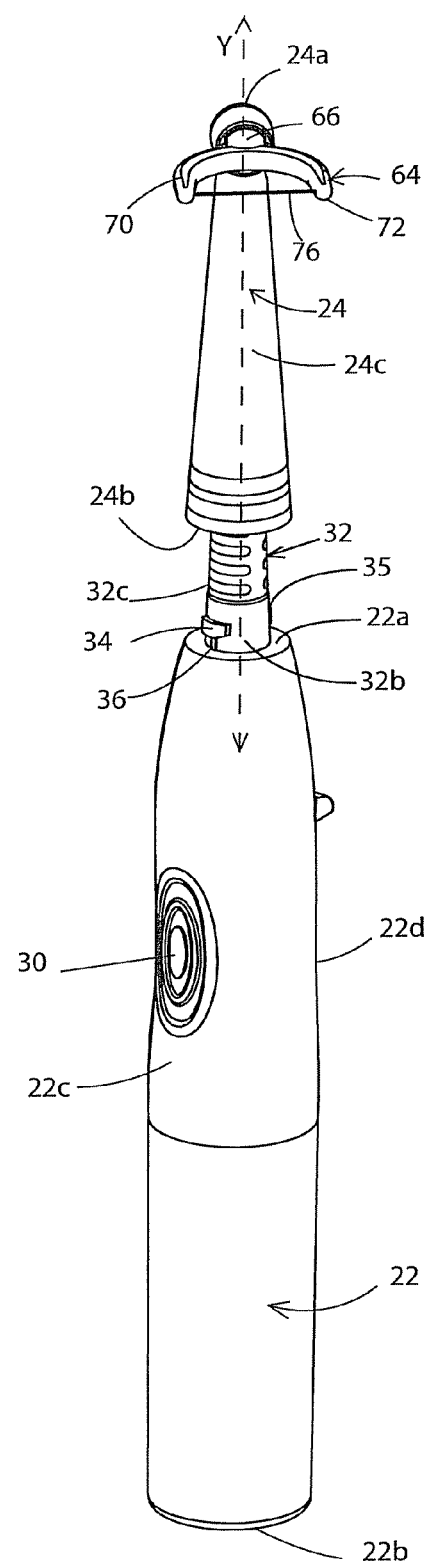
FIG. 3 is a perspective view of the sonic brush in accordance with the present invention, showing the head in an initial engagement position with the handle, and showing the flossing attachment locked to the head.
Figure 4:
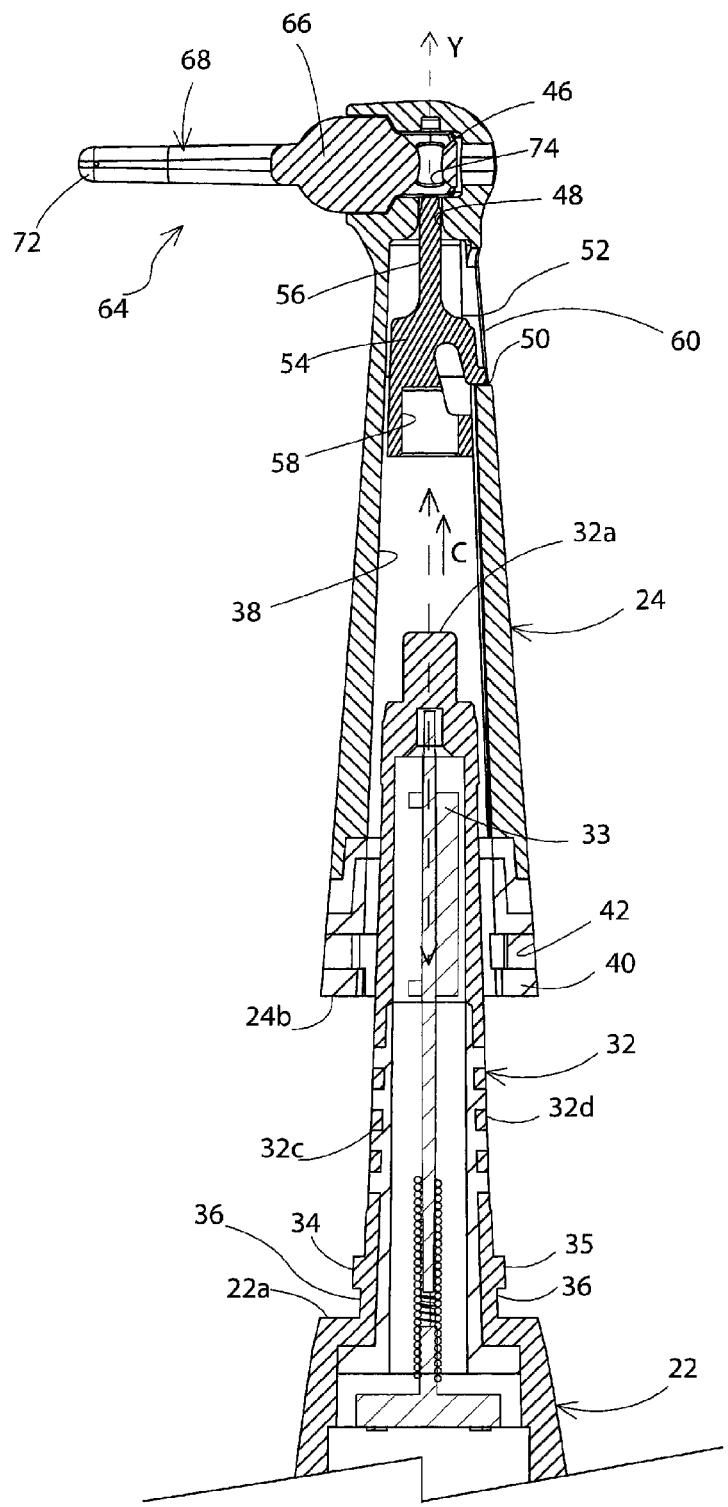
FIG. 4 is a cross-sectional side view of the sonic brush, showing the head disengaged from the handle and the replaceable flossing attachment engaged with the head but not locked thereto.
Figure 5:
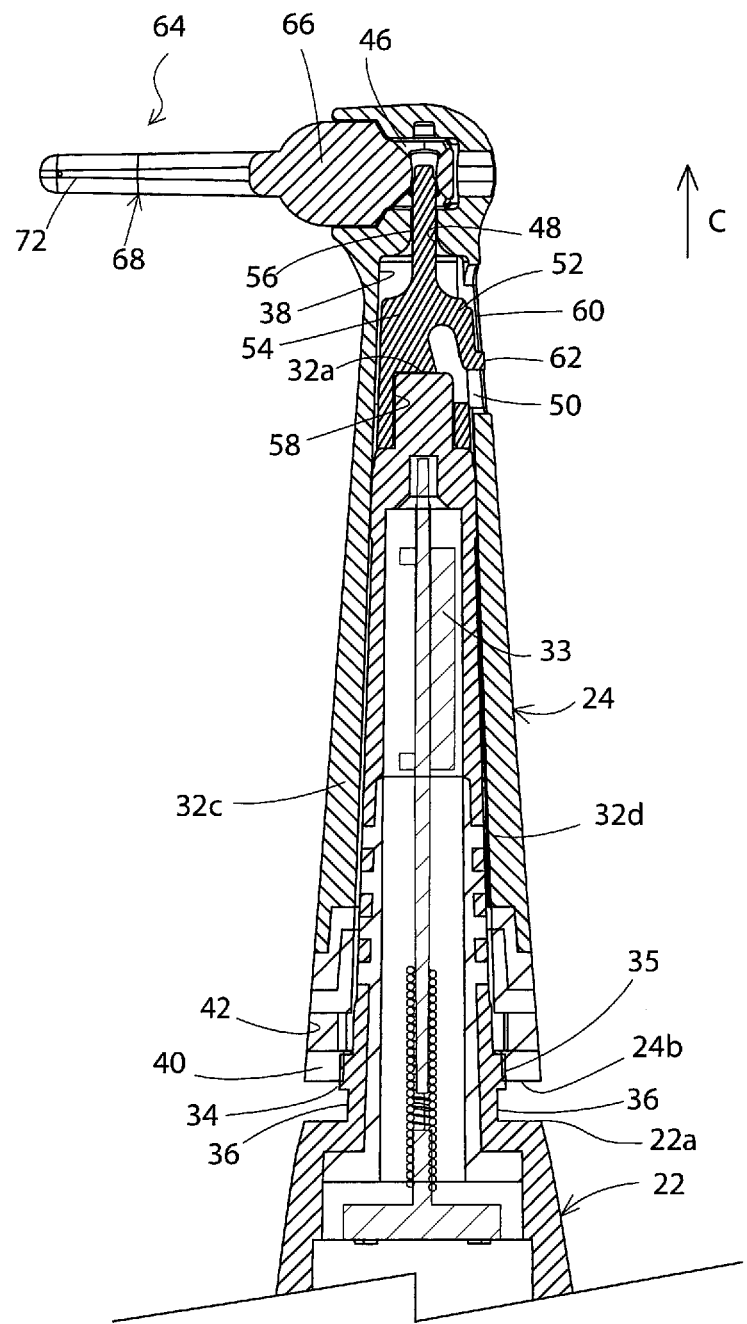
FIG. 5 is a cross-sectional side view of the sonic brush, showing the head initially engaged with the handle but not yet locked thereto; and the flossing attachment engaged with the head but not yet locked thereto.
Figure 6:
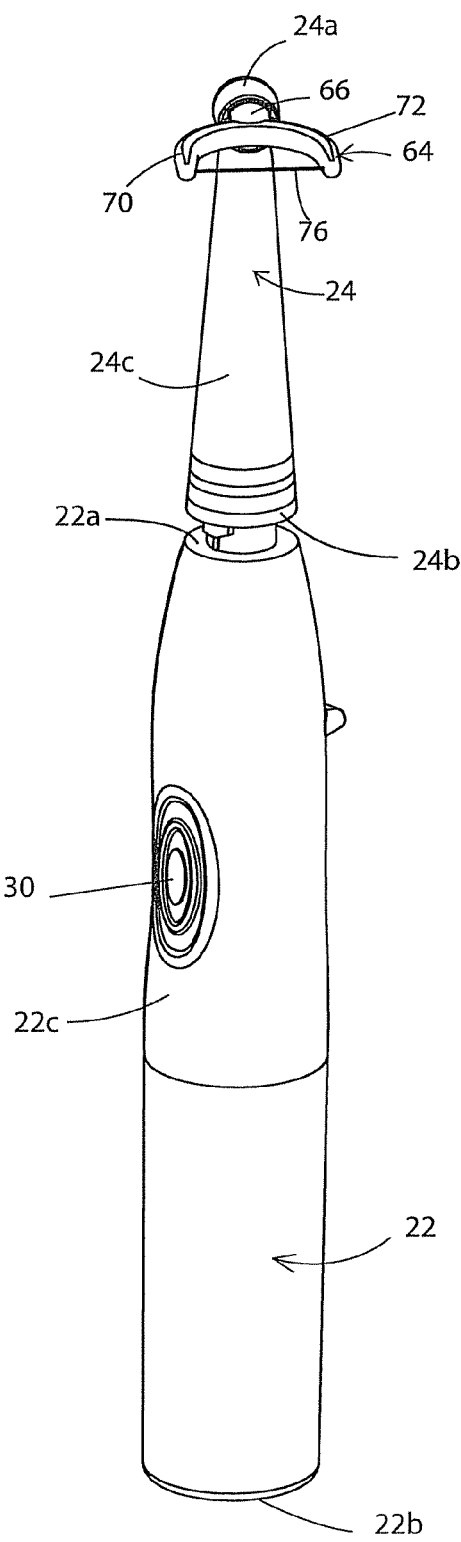
FIG. 6 is a perspective view of the sonic brush with the head in an engaged position with the handle but not yet locked thereto.
Figure 7:
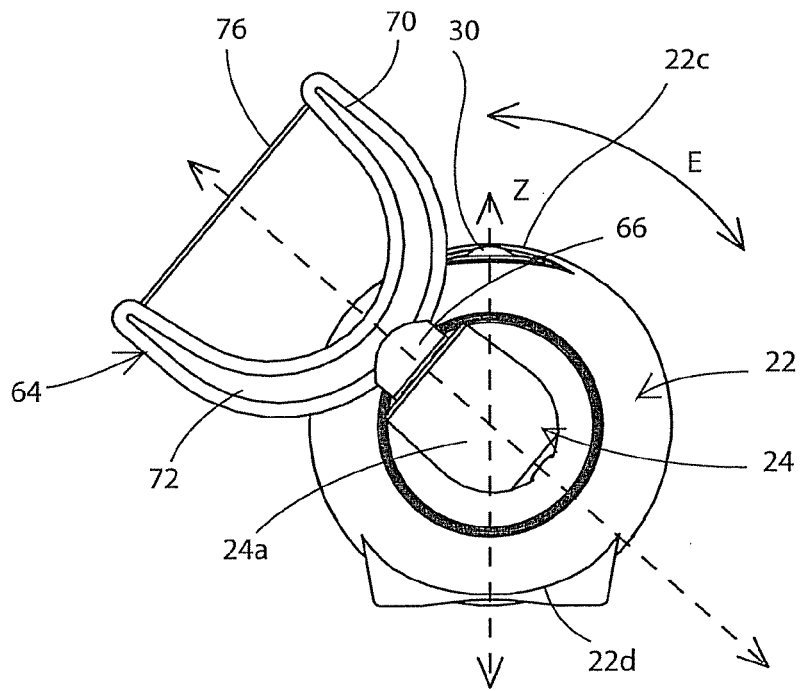
FIG. 7 is a top view of the head shown in the engaged but not yet locked position.
Figure 10:
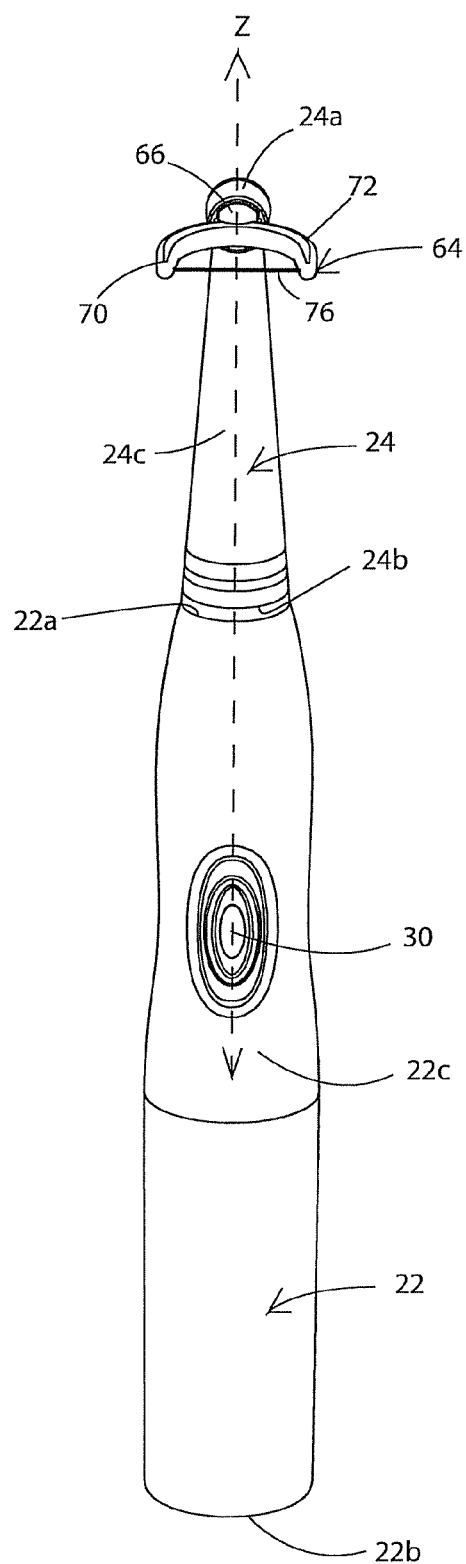
FIG. 10 is a front view of the sonic brush, where the head has been rotated in the locked position with the handle.

The user positions head 24 and handle 22 in the manner indicated in FIG. 3 so that front face 22c of handle 22 and front face 24c of head 24 are offset relative to each other. Top end 32 of attachment member 32 is introduced into interior bore 38 of head 24 (FIGS. 2 & 3) and handle 22 is moved relative to head 24 so that top end 32a advances through bore 38 in the direction of arrow "C" (FIG. 4). The movement is continued until top end 32a of attachment member 32 slides into cavity 58 of locking assembly 52 (FIG. 5). The continued upward movement of attachment member 32 causes locking assembly 52 to slide within bore 38 in the direction of arrow "C" (FIG. 5). The upward motion of locking assembly 52 slides locking pin 56 through channel 48 and into the hole 74 in base 66 of floss hoop 64. The engagement of locking pin 56 in hole 74 locks floss hoop 64 to head 24 but this locked condition is only attained when head 24 is locked to handle 22. Before head 24 and handle 22 are locked together, first and second lock members 34 and 35 are not engaged in first and second recesses 42, 44 and a gap 78 exists between bottom end 24b of head 24 and top end 22a of handle 22 (FIGS. 5 & 6). FIGS. 7 & 8 illustrate the top and bottom views of brush 20 when handle 22 and head 24 are engaged but not locked together. In these figures, the lines "Z" represents a position that is aligned with activation button 30 on front face 22c of handle 22. Line "T" represents a position that is about forty-five degrees out of alignment with line "Z". FIG. 8 shows how first and second lock members 34, 35 are misaligned with the respective first and second recesses 42, 44. The user then rotates one of head 24 and handle 22 relative to the other, as indicated by the arrow "E", so that first and second lock members 34, 35 slide into first and second recesses 42, 44. The gap between head 24 and handle 22 is closed (FIG. 9) and the bottom end 24b of head 24 abuts the top end 22a of handle 22. Furthermore, activation button 30 is aligned with the centerline of floss hoop 64 along line "Z" (FIG. 10).

Figure 11:
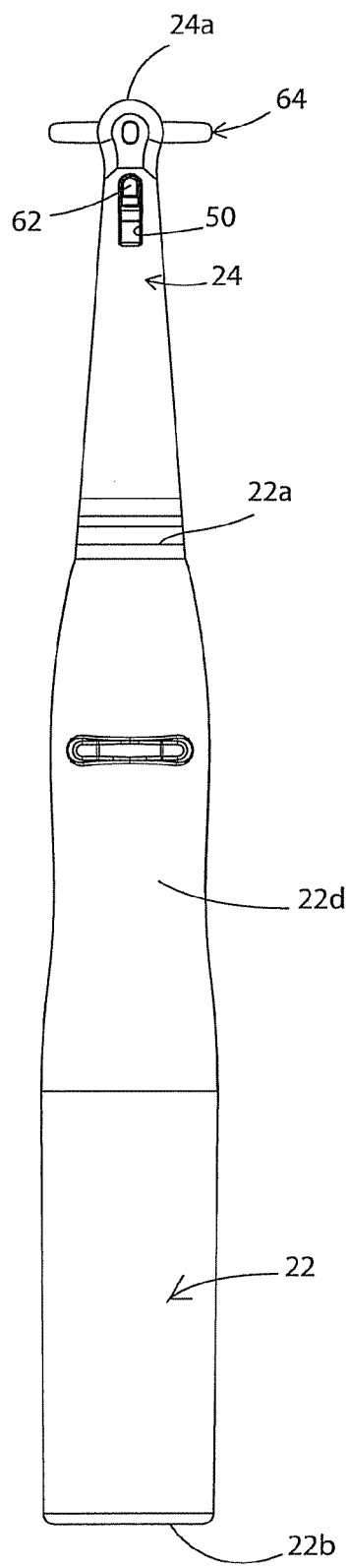
FIG. 11 is a rear view of the sonic brush of FIG. 1, showing the floss attachment button in the locked position.

When head 24 and handle 22 are locked together, the foot 62 of locking assembly 52 protrudes through aperture 50 in rear face 24d of head 24 and is in the position shown in FIG. 11. Because attachment member 32 is engaged in cavity 58 of locking assembly 52, locking assembly 52 is maintained in this locked position and foot 62 cannot be moved downwardly because the attachment member 32 is maintaining the position of locking assembly 52 in bore 38 of head 24. This ensures that dental accessory assembly 64 cannot accidentally become detached from head.

The user is then able to use floss hoop 64 to floss their teeth. This is accomplished by angling brush 20 to insert floss 76 between two adjacent teeth. The activation button 30 is depressed and the vibratory action generator by the vibration mechanism in the handle 22 causes an up and down motion in the floss 76. Because of the extremely rapid vibration generated by the sonic brush 20, the vibratory movement in floss 76 more efficiently removes food and plaque from the teeth than previously known devices.

When it is time to replace head 24, the user simply reverses the order of steps listed above, they rotate head 24 in the opposite direction to remove first and second lock members 34, 35 from first and second recesses 42, 44 and then pull handle 22 in the opposite direction to arrow "C" to withdrawn attachment member 32 from bore 38 of head 24. A different head (not shown) may then be attached to handle 22.

Figure 12:
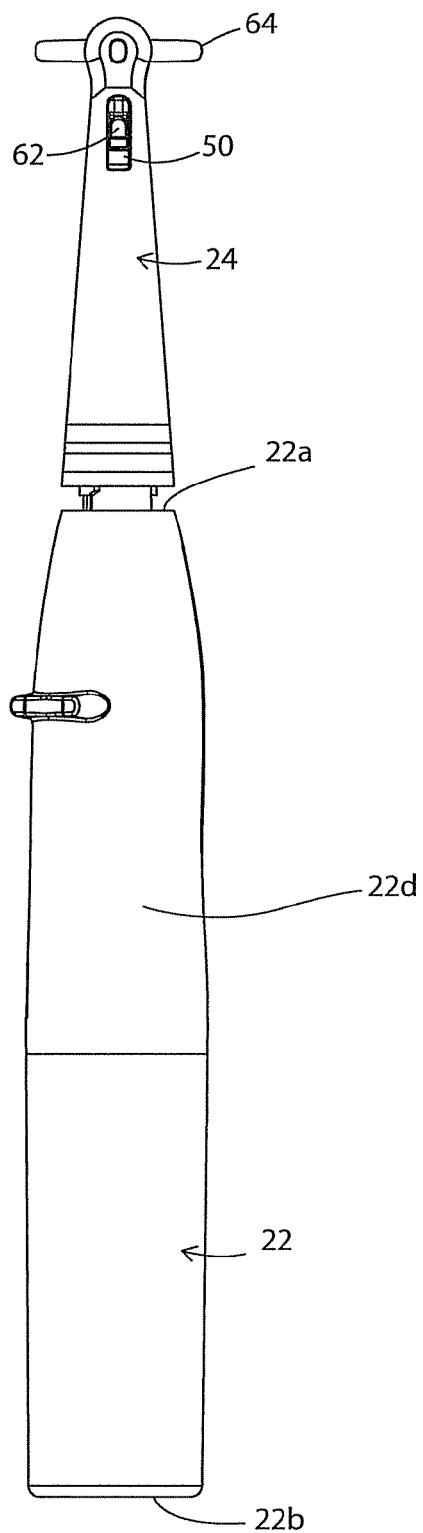
FIG. 12 is a rear view of the sonic brush of FIG. 1, showing the floss attachment button in the unlocked position.
Figure 13:
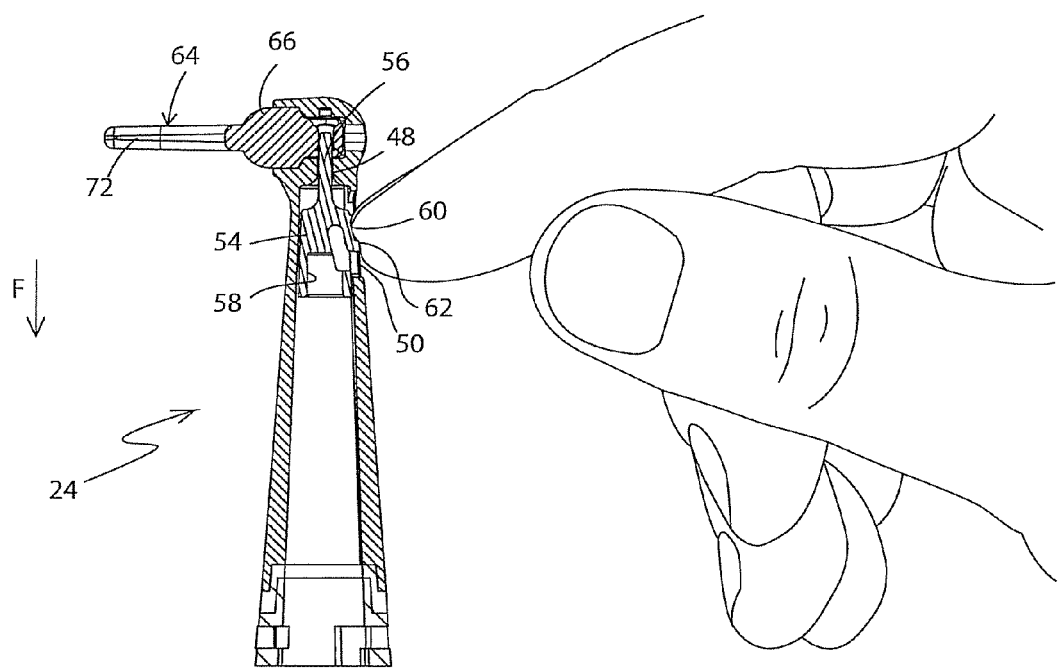
FIG. 13 is a cross-sectional side view of the head of the sonic brush, showing the floss attachment button being engaged to detach the floss attachment from the head.

The user may simply want to replace floss hoop 64. This cannot be done while head 24 is still locked with handle 22. Handle 24 must at least be unlocked from handle 22 so that attachment member 32 does not retain locking assembly 52 in the locked position. FIGS. 11-13 show foot 62 of locking assembly extending slightly outwardly from aperture 50 in rear face 24d of head 24. Using a finger, the user pushes foot 22 downwardly, thereby moving foot 67 from the position shown in FIG. 11 to the position shown in FIG. 12. The downward movement of foot 62, represented by arrow "F" in FIG. 13, slides locking pin 56 out of aperture 76 in base 66 of accessory assembly 64 and through at least a portion of channel 48. This movement breaks the locking connection between accessory assembly 64 and head 24. A new accessory (not shown) may then be inserted into bore 66 and locked into place in the manner previously described.

Figure 14:
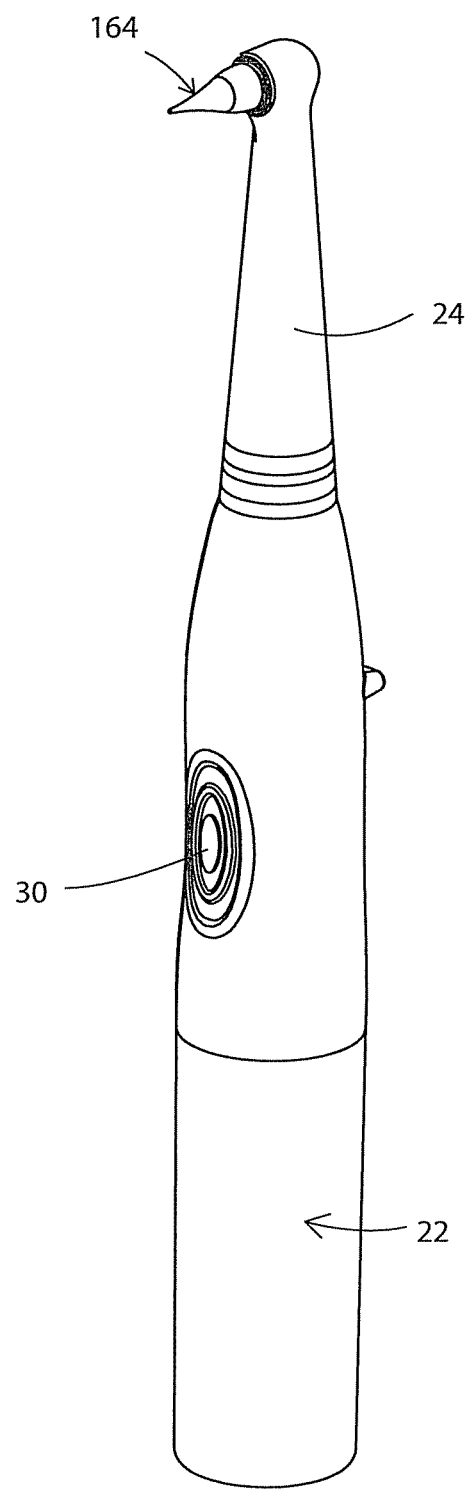
FIG. 14 is a perspective view of the sonic brush of the present invention, showing a second accessory head attached thereto, where the accessory head is a gum stimulator head.
Figure 15:
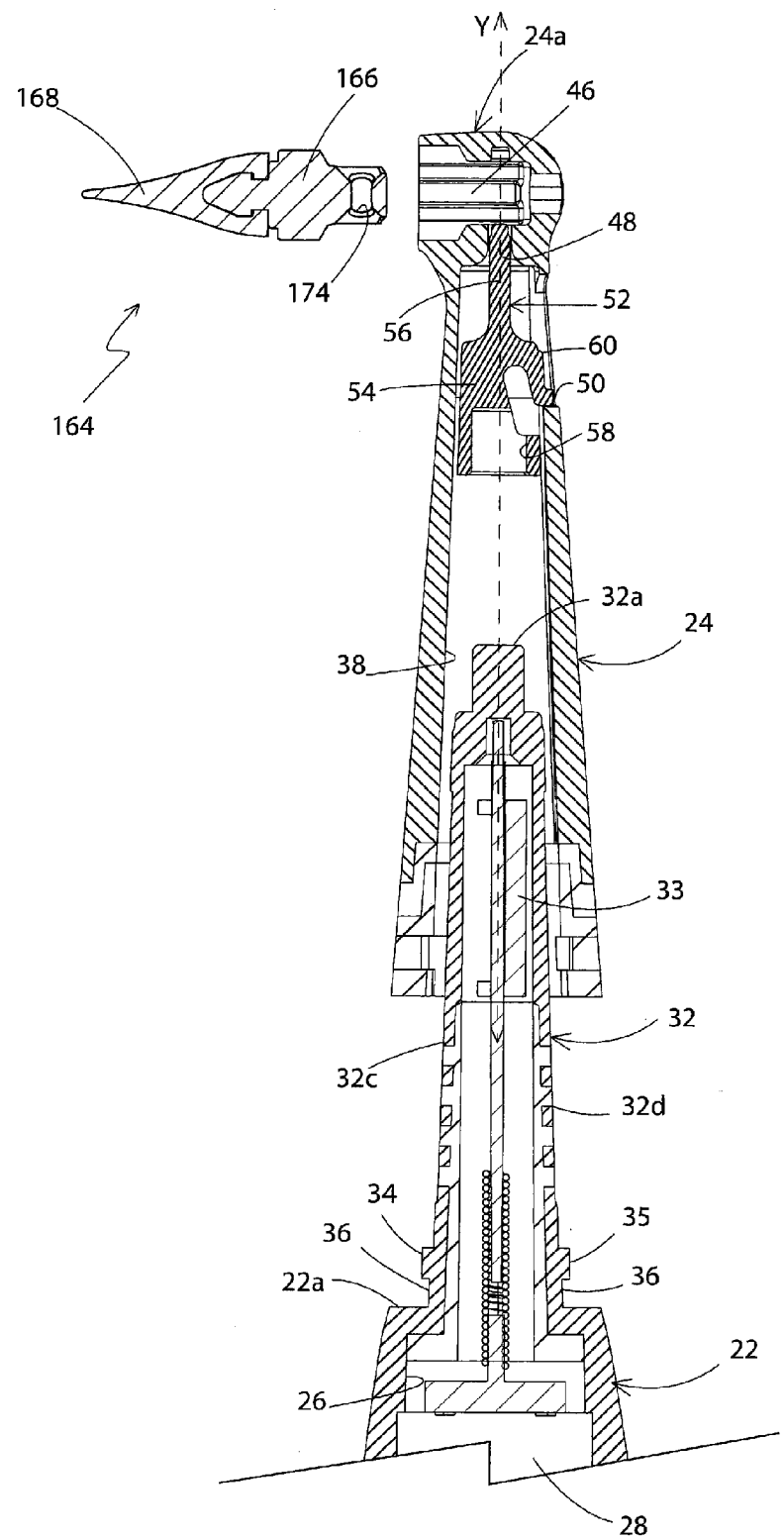
FIG. 15 is cross-sectional side view of a top end of the sonic brush with the head detached from the handle and the accessory head detached from the head.
Figure 16:
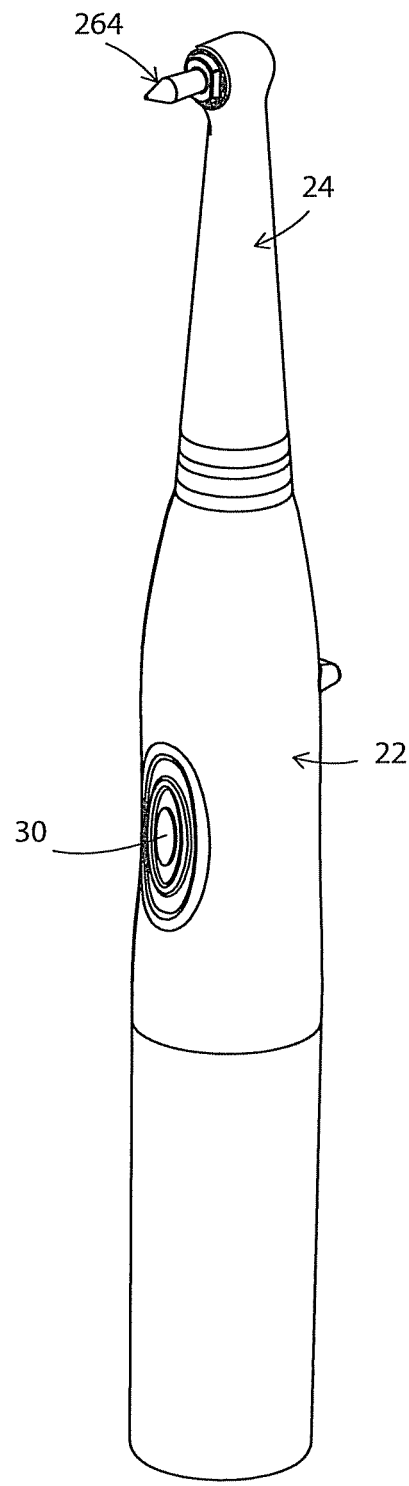
FIG. 16 is a perspective view of the sonic brush of the present invention, showing a third accessory head attached thereto, where the accessory head is an interdental brush.

Referring to FIGS. 14-16, other dental accessory assemblies may be engaged with the head 24 of sonic brush 20. FIG. 14 shows a second dental accessory engaged with head 24, namely, a gum stimulator 164. Gum stimulator 164 includes a base 166 (FIG. 15) having a rubber tip 168 extending outwardly therefrom. Base 166 defines a hole 174 therein that is configured to receive the locking pin 56 of locking assembly 52 therein. The method of engaging and removing gum stimulator 164 is substantially identical to the method of engaging and removing floss hoop 64. When activated, the vibratory mechanism in brush 20 will cause gum stimulator 164 to vibrate up and down rapidly and, when brought into contact with the teeth and gums, will cause food particles and dental plaque to be removed therefrom.

Figure 17:
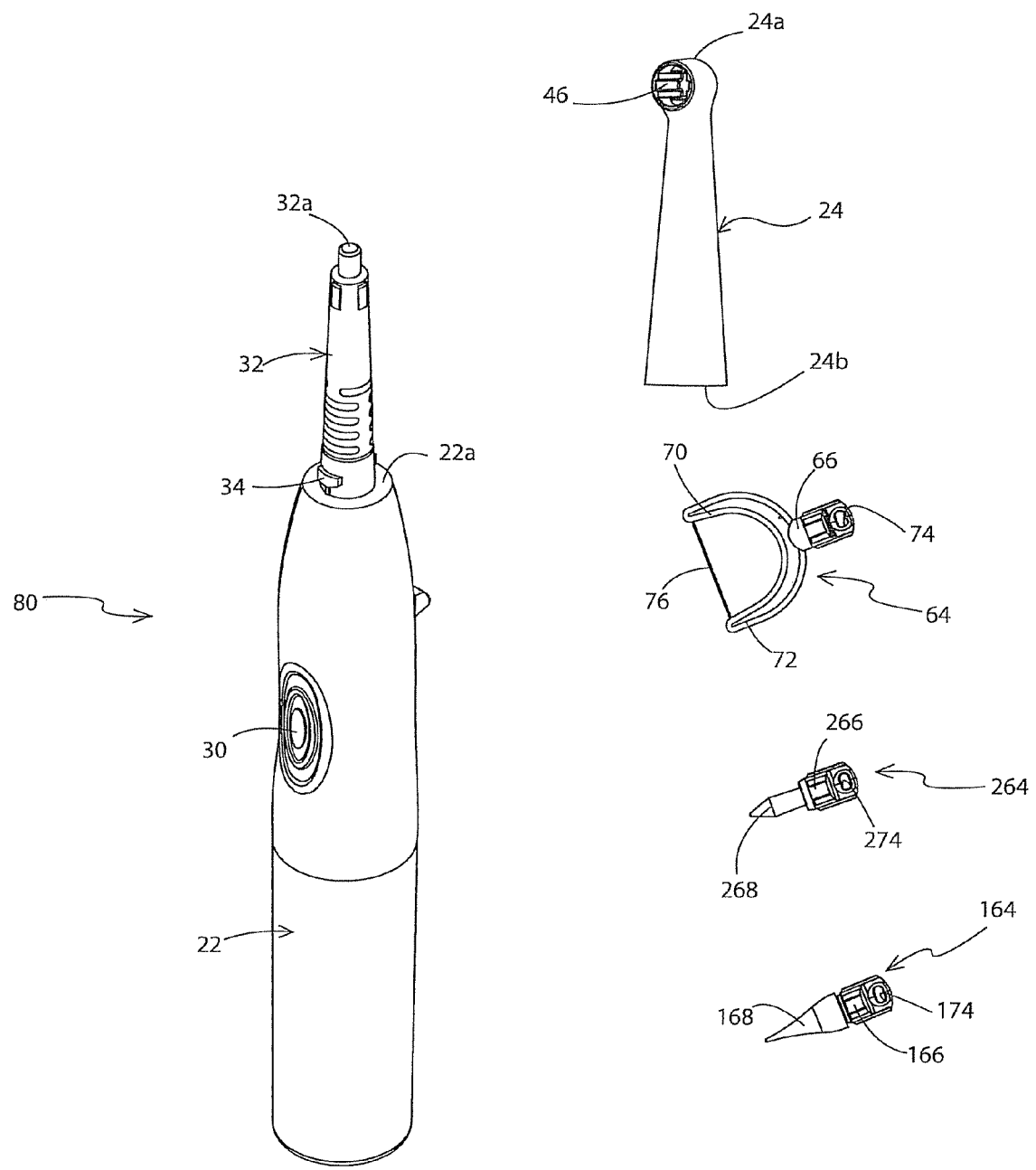
FIG. 17 is a front plan view of a dental hygiene kit that includes a handle, a detachable head, and a plurality of different accessory assemblies for performing different dental hygiene tasks.

In a similar fashion, yet another dental accessory, an interdental cleaning brush 264 (FIG. 16) may be engaged with head 24 and removed therefrom in substantially the same manner as both floss hoop 64 and gum stimulator 164. Cleaning brush 264 includes a base 266 and a plurality of bristles that are configured to form a tip 268. FIG. 17 illustrates that cleaning brush 264 also defines a hole 274 for receiving the locking pin 56 of locking assembly 52 therein. Once again, when the vibratory mechanism is activated, the cleaning brush 264 will vibrate and when tip 268 is positioned between a pair of adjacent teeth, the bristles thereof will cause food particles and dental plaque to be removed from between the teeth and from any surfaces on the teeth which are contacted by the bristles thereof.

Any other type of dental accessory assembly may be engaged and locked into place on head 24 without departing from the spirit of the present invention. These other dental accessory assemblies could include any type of brush head for removing food and plaque from teeth. Additionally, implements for scraping the tongue could also be provided. Any other such dental accessory assemblies will include a base, such as base 66, that may be received and locked into slot 46 in head 24.

As will be evident from the above, the various different dental accessory assemblies 64, 164, 264 may be quickly and easily attached or detached from head 24 so that a user may interchangeably engage the accessory assemblies with the brush and thereby utilize the additional benefit of having that dental accessory vibrated at high speed to remove food and plaque from their teeth. Furthermore, the ease with which the accessory assemblies are connected and disconnected makes it simple to replace the accessory assemblies when they are worn. Additionally, when the accessory assemblies are locked into head 24 by locking pin 56, they cannot be accidentally dislodged, thus aiding in ensuring that the accessory assemblies themselves do not become detached from head 24 during powered flossing or gum stimulation, for example.

It should be noted that while the head may be engaged and locked on the handle without the dental accessory being engaged therewith, it is not possible to engage and lock the dental accessory assemblies to the head without also locking the head to the handle. The reason for this is simply that the locking mechanism for the dental accessory is driven from its unlocked position (FIG. 4) to its locked position (FIG. 9) by the attachment member 32 of handle 22. So, unless the attachment member 32 is used to lock the head and handle together, there is no component available to lock the dental accessory in place.

It will be understood that while the dental accessory assemblies 64, 164 and 264 have been illustrated as mounted substantially at right angles to the longitudinal axis "Y" of brush 20, other mounting locations and orientations could be utilized depending on the type of vibratory mechanism used in brush 20 and the orientation that the dental accessory is best used in the mouth.

Referring to FIG. 17 there is shown a dental care kit 80 that includes handle 22, head 24, and one or more dental care accessory assemblies 64, 164, and 264. As previously described herein, handle 22 includes an attachment member 32 and head 24 is configured to be complementary to attachment member 32 and is engageable therewith. Furthermore, as previously described, head 24 is engaged with handle 22 via attachment member 32 but is not locked thereto until head 24 is rotated through a distance such as a quarter turn. The user is provided with one, two, three or more dental care accessories 64, 164, 264 that are separately and individually selected to be engaged with head 24 so that the user may perform a desired particular type of oral hygiene. So, the user may select the floss pick 64, the gum stimulator 164, or the interdental brush 264, or any other suitable accessory, and then engage that selected accessory assembly with head 24.

As previously describe herein, each accessory assembly 64, 164, 264 includes a respective base 66, 166 or 266 that is receivable in a connector port or slot 46 in head 22. At this point, the accessory assembly is merely engaged with the head 22. It is only when the head 24 is physically locked to the handle 22 by rotating it a quarter turn so that first and second lock members 34, 35 enter first and second recesses 42, 44 that the accessory assembly 64, 164, 166 becomes locked to the head 24. This, of course, occurs when the top end 32a of attachment member 32 enters into cavity 58 of locking mechanism 52 and slides the same through bore 38 of head 24, driving locking pin 56 into the aperture in base 66, 166 or 266 of the then engaged one of the accessory assemblies 64, 164, 264. The locking of head 24 to handle 22 therefore simultaneously results in the locking of the selected one of the accessory assemblies 64, 164, 264 to the head 24. The locking of the selected accessory assembly 64, 164, 264 to head 24 only occurs when the head 24 is locked to the handle 22.

Although not illustrated herein, it will be understood that in addition to the kit 80 including more than one accessory assembly 64, 164, 264, it is also possible to include more than one head 24. Then the user will select one of the plurality of heads 24 and then select one of the accessory assemblies 64, 164, 264 for engagement with the first head and another of the accessory assemblies for engagement with the second head.

Accordingly, brush 20 may be used to perform one or more of a selected group of dental hygiene tasks. The method includes the steps of:

selecting one of a plurality of dental accessory assemblies 64, 164, 264 based on a first one of the dental hygiene tasks;

engaging the selected accessory assembly with a head 24 of a powered toothbrush 20;

engaging the head 24 with a handle 22 that includes a power source and a vibratory mechanism;

locking the head 24 to the handle 22 and thereby locking the selected accessory assembly 64, 164, 264 to the head 22;

positioning the selected accessory assembly adjacent the teeth and gums; and activating the vibratory mechanism to impart vibratory motion to the selected accessory assembly.

The method may further include the steps of:

detaching the head from the handle;

detaching the first selected assembly accessory from engagement with the head;

selecting a second one of the plurality of dental care accessory assemblies;

engaging the second selected accessory assembly with the head;

engaging the head with the handle;

locking the head to the handle and thereby locking the second selected accessory assembly to the head;

positioning the second selected accessory assembly adjacent the teeth and gums; and activating the vibratory mechanism to impart vibratory motion to the second selected accessory assembly so as to perform a second dental hygiene task.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the invention are an example and the invention is not limited to the exact details shown or described.

The invention claimed is:

1. A head for a sonic toothbrush comprising:
   an exterior wall having a top end, a bottom end, a front face and a rear face;
   a bore defined by an interior wall of the head, said bore originating in a bottom face of the head and extending inwardly toward the top end thereof; and wherein the bore is adapted to receive a bayonet mount extending from a handle of the sonic toothbrush; and wherein the bottom end of the exterior wall is adapted to be releasably locked to the handle;
   a recess defined in an interior surface of the interior wall of the head;
   a dental accessory assembly detachably engageable with the exterior wall of the head;
   an aperture defined in the dental accessory assembly; and
   a locking assembly disposed within the bore, wherein a locking pin extends outwardly from the locking assembly, through the aperture in the dental accessory assembly and into the recess in the interior surface of the interior wall of the head when the aperture and recess are aligned, and wherein the locking pin is selectively received within the aperture and recess to selectively lock the dental accessory assembly to the exterior wall of the head;
   the locking assembly is movable between a locked position where the locking pin engages in the aperture in the dental accessory assembly; and an unlocked position where the locking pin is disengaged from the aperture in the dental accessory assembly, and wherein the locking assembly is in the locked position only when the head is locked to the handle;

the locking assembly further includes a mechanism for locking the locking assembly against longitudinal movement within the bore, and the mechanism is movable between a locked and an unlocked position, and when the mechanism is in the unlocked position, the locking assembly is movable in the bore, and when the mechanism is in the locked position, the locking assembly is fixed in position within the bore.

2. The head for a sonic toothbrush as defined in claim 1, wherein the exterior wall of the head defines a slot therein and the dental accessory assembly includes:
a base that is complementary to the slot; and
a dental accessory extending outwardly from the base; and when the locking assembly is in the locked position, the locking pin engages the base and secures the same in the slot, and when the locking assembly is in the unlocked position, the locking pin is disengaged from the base and the base is removable from the slot.

3. The head as defined in claim 1, wherein the dental accessory assembly engages the wall at 90 degrees relative to a longitudinal axis of the exterior wall, where the longitudinal axis extends between the top and bottom ends of the exterior wall.

4. The head as defined in claim 1, wherein the head is adapted to be secured to the handle by rotating the head relative to the handle after the bayonet mount is received in the bore.

5. A head for a sonic toothbrush comprising:
an exterior wall having a top end, a bottom end, a front face and a rear face, and a bore defined by an interior wall of the head, said bore originating in a bottom face of the head and extending inwardly toward the top end thereof; and wherein the bore is adapted to receive a bayonet mount extending from a handle of the sonic toothbrush; and wherein the bottom end is adapted to be releasably locked to the handle; and
a dental accessory assembly that is detachably engaged with the wall; and
a locking assembly that locks the dental accessory assembly to the wall, wherein the locking assembly is movable between a locked position and an unlocked position, wherein the locking assembly is in the locked position only when the head is locked to the handle; and wherein the locking assembly includes a mechanism for locking the locking assembly against longitudinal movement within the bore, and the mechanism is movable between a locked and an unlocked position, and when the mechanism is in the unlocked position, the locking assembly is movable in the bore, and when the mechanism is in the locked position, the locking assembly is fixed in position within the bore.

6. The head for a sonic toothbrush as defined in claim 5, further comprising:
an aperture defined in a rear wall of the head; and
a flexible member extending outwardly from the locking assembly, said flexible member having a terminal end that is received through the aperture and is engageable to move the locking assembly from the locked to the unlocked position.

7. The head as defined in claim 6 wherein said locking assembly travels longitudinally within the bore when the locking assembly is moved between the locked and unlocked positions.

8. The head as defined in claim 7 wherein the locking assembly includes:
a housing sized to be received in the bore of the head;
a cavity defined in the housing; said cavity being adapted to receive a portion of the bayonet mount of the handle therein; and
a locking pin extends outwardly from the housing and into engagement with the base of the dental accessory assembly when the locking assembly is in the locked position.

9. The head as defined in claim 8, further comprising:
an aperture defined in the base of the dental accessory assembly, and wherein a portion of the locking pin is complementary to said aperture, and the portion of the locking pin is received in the aperture when the locking assembly is in the locked position and is withdrawn from the aperture when the locking assembly is in the unlocked position.

10. The head as defined in claim 9, wherein the head has a longitudinal axis that extends between the top end and the bottom end thereof, and the bore in the head is aligned with the longitudinal axis and the locking assembly travels longitudinally within the bore of the head; and wherein a slot is defined in the head and the slot is disposed at right angles to the longitudinal axis; and wherein the base of the dental accessory assembly is disposed within the slot.

11. The head as defined in claim 5, wherein the dental accessory assembly is selected from a group consisting of a floss pick, a gum stimulator and an interdental brush.

12. A toothbrush comprising:
a handle;
a head that is detachably lockable with the handle; and
a dental accessory assembly that is detachably engageable with the head, and wherein the dental accessory assembly is only fixedly secured to the head when the head is locked to the handle, and is removable from the head when the head is unlocked from the handle; and wherein the dental accessory assembly includes:
a base;
a dental accessory extending outwardly from the base in a first direction;
a locking assembly that engages both the head and the base of the dental accessory assembly and releasably secures the same together; and wherein the head defines a bore therein and the locking assembly is disposed within the bore, and the locking assembly includes a locking pin which extends outwardly therefrom and engages in an aperture in the base of the dental accessory assembly and is received into a recess defined in an interior wall of the head; and wherein the locking assembly is movable between a first position where the locking pin is engaged in the aperture in the base of the dental accessory assembly and the recess; and a second position where the locking pin is disengaged from the aperture in the base of the dental accessory assembly;
the locking assembly further includes a mechanism for locking the locking assembly against longitudinal movement within the bore, and the mechanism is movable between a locked and an unlocked position, and when the mechanism is in the unlocked position, the locking assembly is movable in the bore, and when the mechanism is in the locked position, the locking assembly is fixed in position within the bore.

13. The toothbrush as defined in claim 12, wherein the dental accessory is selected from a group consisting of a floss pick, a gum stimulator and an interdental brush.

14. The toothbrush as defined in claim 12, further comprising a vibratory mechanism retained within the handle, and when activated, said vibratory mechanism imparts vibratory movement to the dental accessory assembly.

15. The toothbrush as defined in claim 12, further comprising:
   a first flange disposed on a bottom of the head or a top of the handle; and
   a first recess defined in an other of the bottom of the head and the top of the handle, and wherein the first flange is receivable in the first recess to secure the head and handle together.

16. The toothbrush as defined in claim 15, further comprising:
   a second flange disposed on one of the bottom of the head and the top of the handle; said second flange being spaced from the first flange; and
   a second recess defined in the other of the bottom of the head and the top of the handle, said second recess being spaced from the second flange; and wherein the second flange is receivable in the second recess when the head and handle are secured together.

17. The toothbrush as defined in claim 16, wherein the first flange and first recess are larger than the second flange and second recess.

18. A dental care kit comprising:
   a handle;
   a head configured to engage the handle and to be selectively lockable thereto; wherein the head comprises:
      an exterior wall having a top end, a bottom end, a front face and a rear face, and a bore defined by an interior wall of the head, said bore originating in a bottom face of the head and extending inwardly toward the top end thereof; and wherein the bore receives a bayonet mount extending outwardly from the handle; and wherein the bottom end of the head releasably locks to the handle;
   a plurality of dental care accessory assemblies;
   a connector port provided on the wall of the head, wherein each one of the dental accessory assemblies is selectively separately and individually engageable with the port; and
   a locking assembly is disposed within the bore, wherein a locking pin extends outwardly from the locking assembly and is selectively engageable within an aperture defined in a selected individual dental care accessory assembly and is received into a recess defined in an interior wall of the head, when the aperture is aligned with the recess to lock the accessory to the head; and wherein each of said individual accessory assemblies is only locked to the head when the head is locked to the handle;
      the locking assembly further includes a mechanism for locking the locking assembly against longitudinal movement within the bore, and the mechanism is movable between a locked and an unlocked position, and when the mechanism is in the unlocked position, the locking assembly is movable in the bore, and when the mechanism is in the locked position, the locking assembly is fixed in position within the bore.

19. The dental care kit as defined in claim 18, wherein the plurality of dental care accessory assemblies are selected from a group consisting of a floss pick, a gum stimulator and an interdental brush.

20. The dental care kit as defined in claim 19, wherein each of said individual accessory assemblies is locked simultaneously to the head as the head is locked to the handle.

21. A method of using a toothbrush for performing more than one dental hygiene tasks, said toothbrush comprising a head comprising:
   an exterior wall having a top end, a bottom end, a front face and a rear face, and a bore defined by an interior wall of the head, said bore originating in a bottom face of the head and extending inwardly toward the top end thereof; and wherein the bore is adapted to receive a bayonet mount extending from a handle of the sonic toothbrush; and wherein the bottom end is adapted to be releasably locked to the handle; and
   a plurality of dental accessory assemblies, that is detachably engaged with the wall; and
   a locking assembly that locks one of the dental accessory assemblies to the wall, wherein the locking assembly is movable between a locked position and an unlocked position, and wherein the locking assembly is in the locked position only when the head is locked to the handle; and wherein the locking assembly includes a mechanism for locking the locking assembly against longitudinal movement within the bore, and the mechanism is movable between a locked and an unlocked position, and when the mechanism is in the unlocked position, the locking assembly is movable in the bore, and when the mechanism is in the locked position, the locking assembly is fixed in position within the bore, and
said method including the steps of:
   selecting one of said plurality of dental accessory assemblies based on a first one of the dental hygiene tasks;
   engaging the selected accessory assembly with the head of the powered toothbrush;
   engaging the head with the handle that includes a power source and a vibratory mechanism;
   locking the head to the handle and thereby moving a locking pin on the locking assembly disposed within the bore in the head into an aperture defined in the selected accessory assembly and subsequently into a recess defined in the interior wall of the head; and thereby locking the selected accessory assembly to the head;
   positioning the selected accessory assembly adjacent a user's teeth and gums; and
   activating the vibratory mechanism to impart vibratory motion to the selected accessory assembly.

22. The method as defined in claim 21, further comprising the steps of:
   detaching the head from the handle;
   detaching the first selected accessory assembly from engagement with the head by withdrawing the locking pin of the locking assembly from its engagement with the first selected accessory assembly;
   selecting a second one of the plurality of dental care accessory assemblies;
   engaging the second selected accessory assembly with the head;
   engaging the head with the handle;
   locking the head to the handle by moving the locking pin on the locking assembly into an aperture in the second accessory assembly and thereby locking the second selected accessory assembly to the head;
   positioning the second selected accessory assembly adjacent the user's teeth and gums; and
   activating the vibratory mechanism to impart vibratory motion to the second selected accessory assembly in order to perform a second dental hygiene task.

* * * * *